US012282590B1

(12) United States Patent
Sanders et al.

(10) Patent No.: US 12,282,590 B1
(45) Date of Patent: Apr. 22, 2025

(54) BIOMETRIC SYSTEM AND METHOD

(71) Applicant: Sony Interactive Entertainment Inc., Tokyo (JP)

(72) Inventors: Matthew Sanders, London (GB); Richard Downey, London (GB); Oliver Hume, London (GB); Michael Karl Werle, London (GB)

(73) Assignee: Sony Interactive Entertainment Inc., Tokyo (JP)

( * ) Notice: Subject to any disclaimer, the term of this patent is extended or adjusted under 35 U.S.C. 154(b) by 0 days.

(21) Appl. No.: 18/317,253

(22) Filed: May 15, 2023

(30) Foreign Application Priority Data

May 18, 2022 (GB) ..................... 2207276

(51) Int. Cl.
*G06F 3/01* (2006.01)
*A63F 13/21* (2014.01)
*A63F 13/24* (2014.01)

(52) U.S. Cl.
CPC ............... *G06F 3/01* (2013.01); *A63F 13/21* (2014.09); *A63F 13/24* (2014.09)

(58) Field of Classification Search
CPC ............. A63F 13/21; A63F 13/24; G06F 3/01
See application file for complete search history.

(56) References Cited

U.S. PATENT DOCUMENTS

| 8,699,020 B1 * | 4/2014 | Zhou ...................... G01N 21/65 356/301 |
| 2007/0167836 A1 | 7/2007 | Scepanovic |
| 2007/0200663 A1 * | 8/2007 | White ................... B60R 25/255 340/5.31 |
| 2010/0030480 A1 | 2/2010 | Wolfgang |
| 2017/0135633 A1 | 5/2017 | Connor |
| 2018/0116605 A1 * | 5/2018 | Newberry ............... A61B 5/01 |
| 2018/0250585 A1 | 9/2018 | Weissman |
| 2021/0342020 A1 | 11/2021 | Jorasch |
| 2023/0277063 A1 * | 9/2023 | Cucinelli ............. A61B 5/6801 600/310 |

FOREIGN PATENT DOCUMENTS

| CN | 201084118 Y | * | 7/2008 |
| CN | 101310805 A | | 11/2008 |
| CN | 105117040 A | * | 12/2015 |

(Continued)

OTHER PUBLICATIONS

Extended European Search Report for corresponding EP Application No. 23171301.7, 10 pages, dated Jul. 28, 2023.

(Continued)

*Primary Examiner* — Ricardo Osorio
(74) *Attorney, Agent, or Firm* — Kilpatrick Townsend & Stockton LLP

(57) ABSTRACT

A user input device includes an optical window facing onto a region of skin of the user when the user input device is in normal use, a monochromatic light source arranged to emit light through the optical window, a spectral dispersal unit adapted to disperse the spectrum of light reflected back from the region of skin of the user, the reflected light no longer being wholly monochromatic due to Raman scattering, and a light sensor operable to detect at least some of the dispersed spectrum of light and output corresponding light data.

13 Claims, 4 Drawing Sheets

(56) References Cited

FOREIGN PATENT DOCUMENTS

| | | | | | |
|---|---|---|---|---|---|
| CN | 205594601 | U | * | 9/2016 | |
| CN | 206805486 | U | * | 12/2017 | |
| CN | 207020083 | U | * | 2/2018 | ............. G01N 21/65 |
| CN | 207718340 | U | * | 8/2018 | |
| CN | 113492865 | A | | 10/2021 | |
| CN | 216792851 | U | * | 6/2022 | |
| EP | 3505051 | A1 | * | 7/2019 | ........... A61B 5/0002 |
| JP | 2000010731 | A | * | 1/2000 | |
| KR | 102313630 | B1 | | 10/2021 | |
| WO | 2013006620 | A2 | | 1/2013 | |
| WO | WO-2018103943 | A1 | * | 6/2018 | ........... A61B 5/0075 |
| WO | 2022032218 | A1 | | 2/2022 | |
| WO | WO-2022084539 | A2 | * | 4/2022 | ........... A61B 5/0075 |

OTHER PUBLICATIONS

Combined Search and Examination Report for corresponding GB Application No. 2207276.3, 6 pages, dated Nov. 21, 2022.
"Raman Spectroscopy", Available online at: https://en.wikipedia.org/w/index.php?title=Raman_spectroscopy&oldid=1085187452, Apr. 28, 2022, pp. 1-23.
EP23171301.7 , "Office Action", Jul. 10, 2024, 13 pages.
Communication pursuant to Article 94(3) EPC for corresponding application No. EP23171301.7, 15 pages, Jan. 10, 2025.

* cited by examiner

BIOMETRIC SYSTEM AND METHOD

BACKGROUND OF THE INVENTION

The present invention relates to a biometric system and method.

DESCRIPTION OF THE PRIOR ART

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Systems for characterising the status of an individual, such as drowsiness or stress levels, typically use a particular biometric sensor such as a heart monitor, EEG monitor, or camera with image analysis (for example to monitor eye behaviours).

However, such systems are thus typically either complex (for example in the case of the camera and analysis of the user's appearance/behaviour), or require active voluntary participation by the user (for example to wear the heart or EEG monitor), and occasions when a user are tired or stressed are the most likely times when the user may not correctly or fully comply with the requirements for such systems to work.

As a result such a system may either fail to work, which may be inconvenient or dangerous, or may default to a fail-safe, which itself may be inconvenient.

Embodiments of the present description seem to mitigate or alleviate this problem.

SUMMARY OF THE INVENTION

Various aspects and features of the present invention are defined in the appended claims and within the text of the accompanying description.

In a first aspect, a user input device is provided in accordance with claim 1.

In another aspect, a biometric system is provided in accordance with claim 8.

In another aspect, a biometric method is provided in accordance with claim 13.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DESCRIPTION OF THE EMBODIMENTS

A biometric system and method are disclosed. In the following description, a number of specific details are presented in order to provide a thorough understanding of the embodiments of the present invention. It will be apparent, however, to a person skilled in the art that these specific details need not be employed to practice the present invention. Conversely, specific details known to the person skilled in the art are omitted for the purposes of clarity where appropriate.

Figure 1:
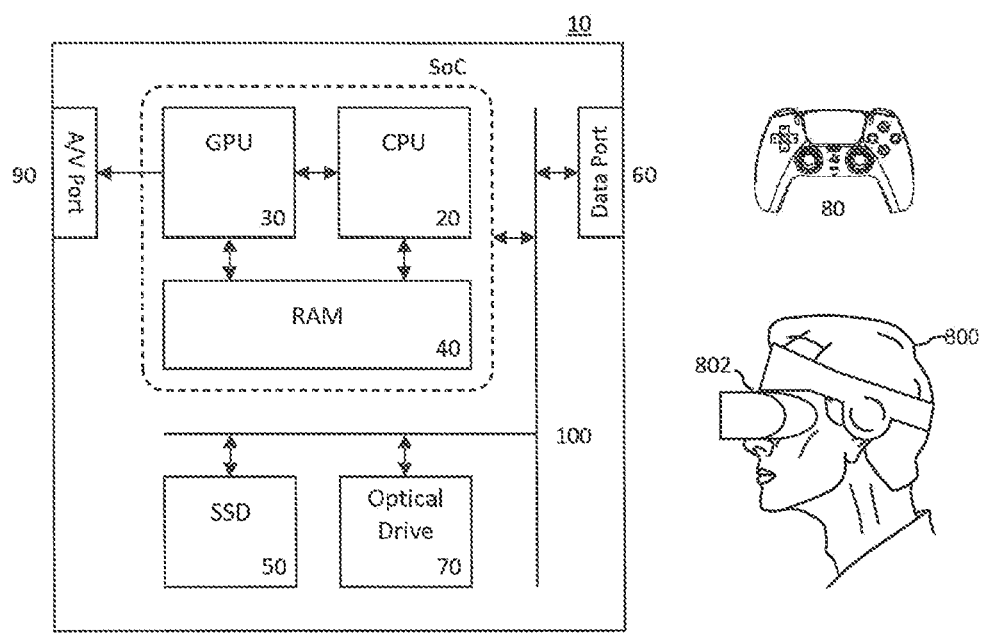
FIG. 1 is a schematic diagram of a biometric system in accordance with embodiments of the present description.

Referring now to the drawings, wherein like reference numerals designate identical or corresponding parts throughout the several views, FIG. 1 shows an example of an entertainment system 10 (a computer or console such as the Sony® PlayStation 5® 'PS5').

The entertainment system 10 comprises a central processor 20. This may be a single or multi core processor, for example comprising eight cores as in the PS5. The entertainment system also comprises a graphical processing unit or GPU 30. The GPU can be physically separate to the CPU, or integrated with the CPU as a system on a chip (SoC) as in the PS5.

The entertainment device also comprises RAM 40, and may either have separate RAM for each of the CPU and GPU, or shared RAM as in the PS5. The or each RAM can be physically separate, or integrated as part of an SoC as in the PS5. Further storage is provided by a disk 50, either as an external or internal hard drive, or as an external solid state drive, or an internal solid state drive as in the PS5.

The entertainment device may transmit or receive data via one or more data ports 60, such as a USB port, Ethernet® port, WiFi® port, Bluetooth® port or similar, as appropriate. It may also optionally receive data via an optical drive 70.

Interaction with the system is typically provided using one or more handheld controllers 80, such as the DualSense® controller in the case of the PS5.

Audio/visual outputs from the entertainment device are typically provided through one or more A/V ports 90, or through one or more of the wired or wireless data ports 60.

Where components are not integrated, they may be connected as appropriate either by a dedicated data link or via a bus 100.

An example of a device for displaying images output by the entertainment system is a head mounted display 'HMD' 802, worn by a user 800.

Figure 2:
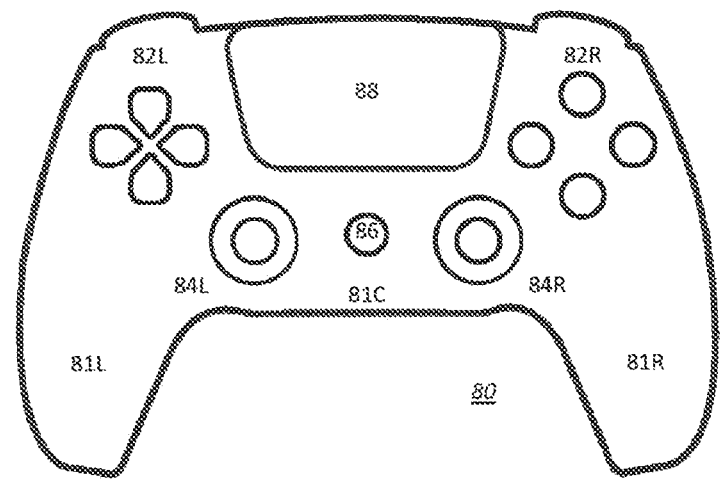
FIG. 2 is a schematic diagram of a user input device.

Referring now to FIG. 2, a handheld controller may take one of a number of forms. Non-limiting examples include a wand-style controller such as the Sony PlayStation Move®, a joystick (which may be held freely in the hand or mounted on a fixed mount), a steering wheel (which again may be held freely in the hand or mounted on a fixed mount), or a handheld controller such as the DualSense® controller 80 shown in FIG. 2. References to a handheld controller or the DualSense® controller herein may be taken to encompass other handheld controllers such as those listed above unless otherwise specified.

Similarly as will be described later herein, some functions of a handheld controller 80 may be performed by a head-mounted display 802, and so references a handheld controller or the DualSense® controller herein may be taken to encompass a head mounted display as appropriate.

In FIG. 2, the DualSense® controller 80 is illustrated as an example of a handheld controller. Such a controller typically has two handle sections 81L, R and a central body 81C. Various controls are distributed over the controller, typically in local groups. Examples include a left button group 82L, which may comprise directional controls and/or one or more shoulder buttons, and similarly right button group 82R, which comprise function controls and/or one or more shoulder buttons. The controller may also include left and/or right joysticks 84L, R, which may optionally also be operable as buttons. The controller (typically in the central portion of the device) may also comprise one or more system buttons 86, which typically cause interaction with an operating system of the entertainment device rather than with a game or other application currently running on it; such buttons may summon a system menu, or allow for recording or sharing of displayed content. Furthermore, the controller may comprise one or more other elements such as a touchpad 88, a light for optical tracking (not shown), a screen (not shown), haptic feedback elements (not shown), and the like.

Figure 3:
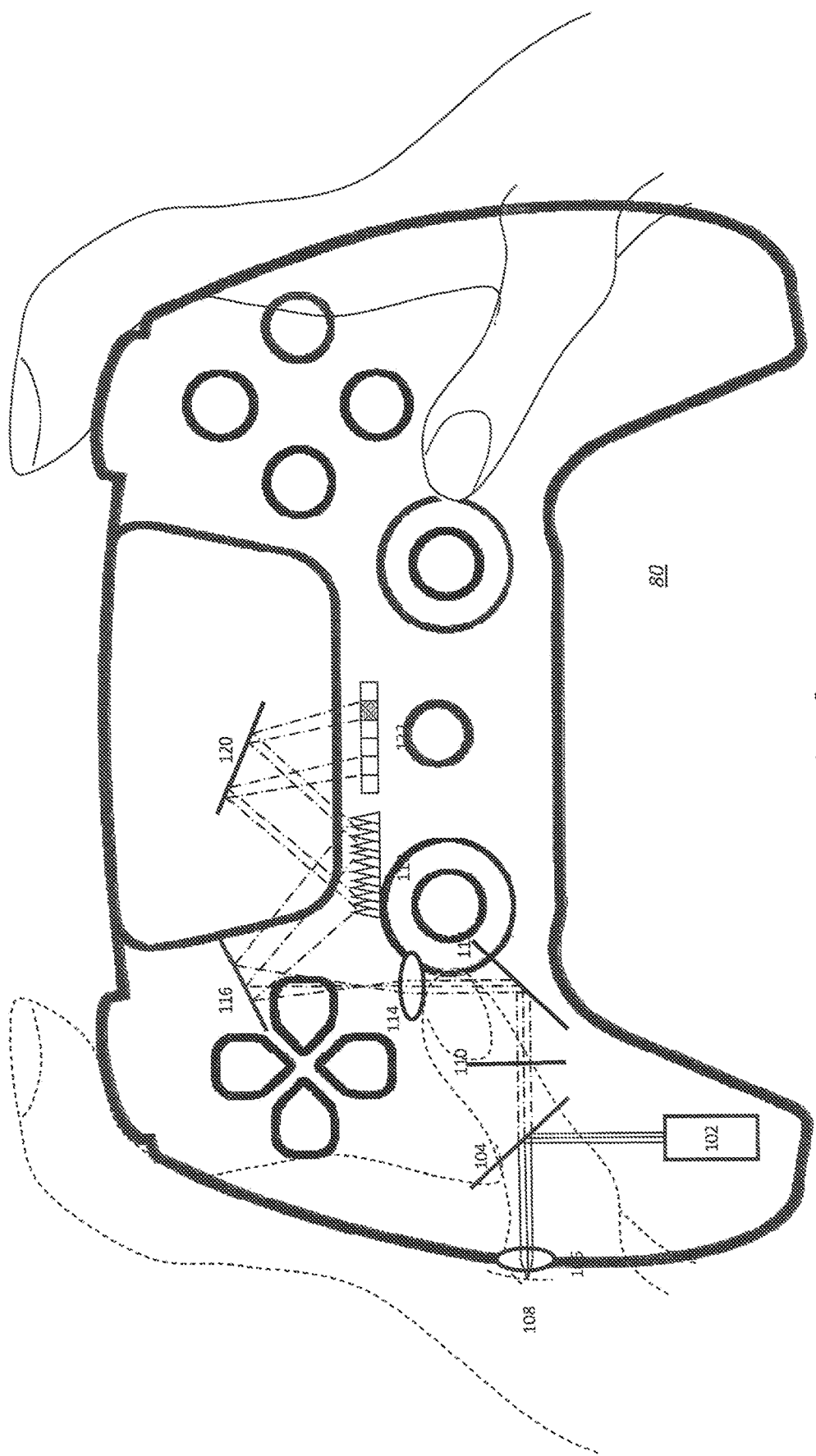
FIG. 3 is a schematic diagram of a user input device in accordance with embodiments of the present description.

Turning now to FIG. 3, in embodiments of the present description the handheld controller 80 (and/or head mounted display) comprises a biometric system for analysing sweat using spectroscopy. This is advantageous as it does not require consumable components or rely on chemical reactions.

The approach is to use a laser source to illuminate a portion of the user's skin. Being a monochromatic source, almost all the light that is scattered by the skin is at the source wavelength. However, a very small proportion is scattered at different colours due to interactions of the light with molecules on the skin's surface, and in particular in their sweat. The wavelengths of these colours each correspond to the vibration of a particular molecular bond, and is known as Raman scatter.

Because the light source is monochromatic, the spectrum of Raman scattered light can be directly attributed to specific chemical signatures for various molecules, including hormones such as cortisol (which can indicate stress), metabolites such as glucose (indicative of blood sugar levels), and electrolytes such as sodium or potassium, which could indicate dehydration. Other common compounds that may be of relevance include lactate, which can indicate muscle fatigue and/or low oxygenation. Other fatty acids and proteins can also be indicators of stress. One or more such chemical compounds may be detected using this technique.

In embodiments of the present description, a full spectroscopic analysis of an arbitrary chemical sample is not required. The system may be set up to detect just one chemical signature, or optionally two, or further optionally three. However the principle is not limited to this (for example it could detect the five compounds mentioned above), but becomes more complex as the number of chemicals to detect increases.

Typically the spectrum of Raman scattered light provides a chemical signature based on the position and relative levels of peaks within the spectrum. Meanwhile the overall level of the spectrum is proportional to the concentration of the target material.

For a system that is designed to measure one kind of surface material (skin) and only one or a small number of chemical signatures on it (e.g. cortisol and/or glucose), the spectra are therefore relatively straightforward to detect.

FIG. 3 illustrates one possible arrangement of an optical Raman scatter and measurement system for a handheld controller. It will be appreciated that different layouts of such a system may be appropriate for different types of handheld controller, and that different forms of such a system (for example with more or fewer mirrors, more or fewer lenses, and/or components not seem in FIG. 3 such as light guides or optical fibres) may be considered within the scope of such a system, provided they adhere to the basic principle that light from a monochromatic source is reflected from a target surface, and the resulting spectrum of reflected light is dispersed to spatially separate colours therein before being imaged on a sensor such as a CMOS or similar digital image sensor for measurement.

In FIG. 3, a monochromatic light source such as a laser 102 emits light towards partial mirror 104, which reflects the light to lens 106. The lens projects the light onto user skin 108, which is pressed against the lens (or a window, not shown, in the housing of the controller if the lens itself is not mounted in the housing as a window), during normal use of the controller. Light is reflected back from the user's skin, including light at additional frequencies due to Raman scattering as described previously herein, and passes through partial mirror 104 and subsequently through a filter 110 for removing unwanted scattered light and/or ambient light. Hence this filter may remove or reduce the original monochromatic light, for example.

The light may then be reflected or guided as needed, for example by mirror 112, through a second lens 114 and mirror 116 to spread the light onto a diffraction grating 118 or other means of spectral dispersion of light. The spectral dispersion means may be essential one-dimensional, e.g. dispersing the spectrum on one axis, or two-dimensional e.g. dispersing the spectrum on two axes, as appropriate.

The dispersed light may then be reflected or guided as needed, for example by mirror 120, to a light sensor 122 such as a CMOS digital imaging sensor, which measures the received light. The sensor may be adapted or selected for example in response to the type of spectral dispersion means; for example a non-square CMOS sensor may have its long axis aligned with a one-dimensional dispersion, or with the axis with the largest dispersion in a two-dimensional dispersion. Similarly sensors with different resolutions may be chosen responsive to the degree of dispersion achieved by the spectral dispersion means and any intervening light path to the sensor.

As noted elsewhere herein this is an illustrative and non-limiting example of the optical components of the measurement system. More, fewer, and/or alternative components may be used, for example to position one or more of the laser source, spectral dispersion means, and light sensor within available spaces within an existing (or adapted) controller layout.

Similarly more, fewer, and/or alternative components may be used depending on available space, cost, number of signatures required to detect, and the like.

Figure 4:
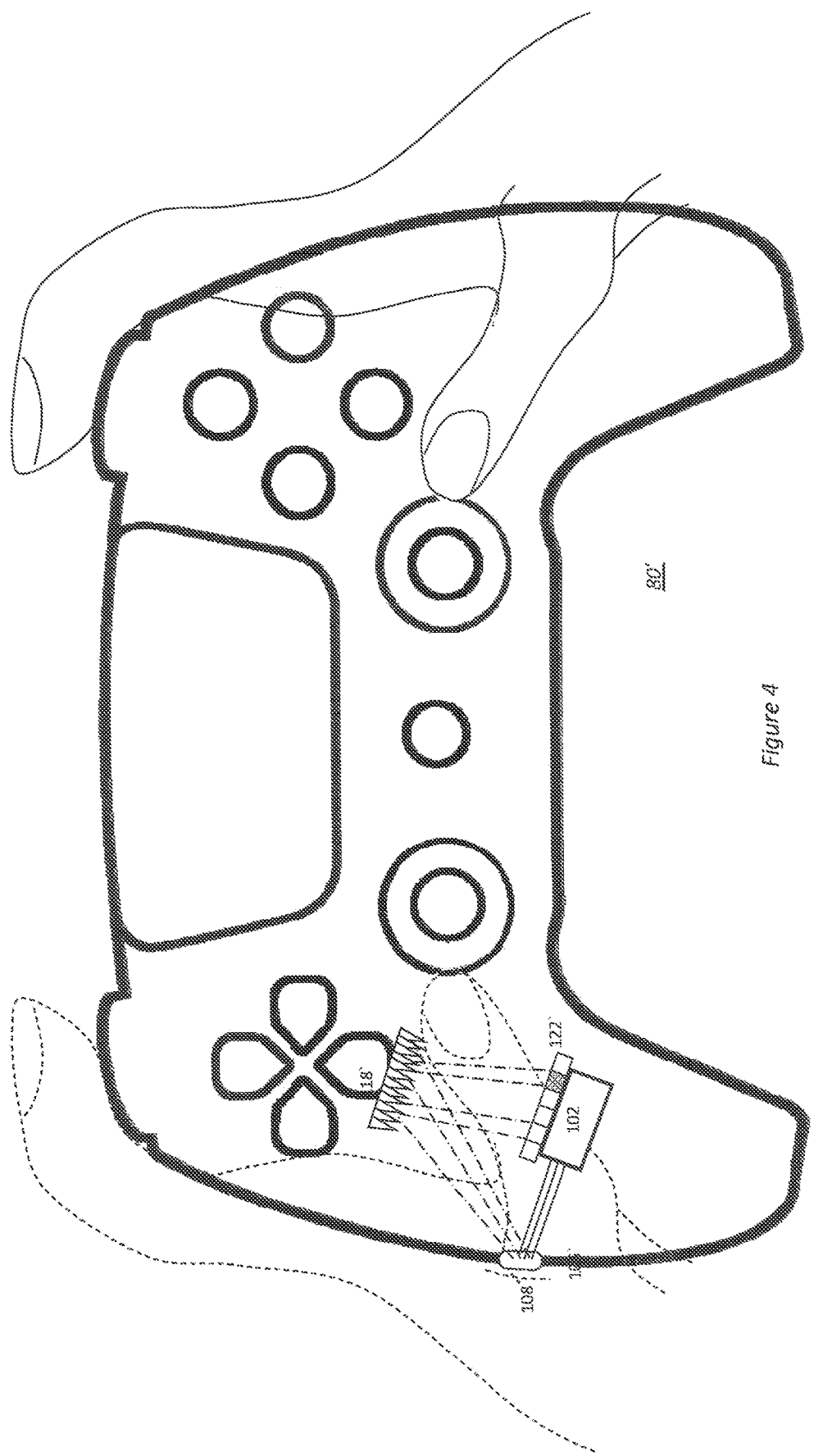
FIG. 4 is a schematic diagram of a user input device in accordance with embodiments of the present description.

Hence for example FIG. 4 illustrates an alternative non-limiting example hand-held controller 80' based on similar principles, in which the monochromatic light source 102 is directed at a non-orthogonal angle to a window 106' (which may have a lensing function, and if so this may be different to that in FIG. 3). The light reflects off the user's skin 108 directly towards spectral dispersion means 118', which may be a different diffraction grating or other spectral dispersion means to that in FIG. 3. The dispersed light is then imaged directly by sensor 122', which may be a different sensor to that in FIG. 3, and in turn may require modified subsequent analysis (for example digitally filtering or discounting the monochromatic source from the measurements, in the absence of a physical filter 110).

In either case, the measurement process can use a sufficiently long exposure to collect sufficient light for a statistically significant analysis of the target spectrum/spectra, and repeat this periodically to track the target compound(s) on the user's skin/in the user's sweat over time. This periodicity may be continuous (e.g. ongoing exposure cycles) or every N seconds or minutes.

The system can optionally detect if a given measurement has been spoiled, for example by detecting if the measured spectrum is much brighter than expected, or contains colours inconsistent with Raman scattering, due to ambient light entering the lens/window 106 in the housing. Alternatively or in addition this may be detected by a photodiode or similar located near the lens/window, thereby saving the computational effort of analysing the measurement to detect this.

Optionally a threshold amount or proportion of ambient light may be tolerable and still allow the measurement of one or more target compounds. In this case the measured spectrum or the signal from the photodiode as applicable may be compared to such a threshold to determine whether the resulting measurement can be used.

The measurement may be analysed by an analysis processor in the handheld controller, or may be transmitted (for example using the same communication path as other inputs from the controller) to the entertainment device or more generally whatever system receives and uses the control inputs from the user, and a processor of that device or system may similarly operate as the analysis processor.

The relative peak positions and levels for one or more compounds may be detected by an analysis of the data from the light sensor 122. One or more target spectra for each of one or more target compounds may be stored for comparison. One compound may have plural spectra stored to accommodate incidental variations in the compound, or common contaminations of the compound (for example the spectrum for a target hormone such as cortisol may have different target spectra that also account for overlapping peaks due to other common chemicals or hormones, which may be at different concentrations for example due to the user's age or gender). A similar approach may be used for target metabolites such as glucose, or lactate.

The analysis by the analysis processor (or 'compound identification processor') will typically be based on a one or two dimensional image captured by the light sensor, depending on the nature of the spectral dispersion means. For a one-dimensional dispersion, the detected signals on a line orthogonal to the dispersion direction (optionally within a subset of the line centred on the expected axis of illumination) can be summed to a single value to increase sensitivity and allow for temporary or permanent misalignment of the optical path. The single values thus obtained for each line along the sensor then form the spectrum measurement.

For a two-dimensional dispersion, the detected signals will form an image with different regions illuminated on an x-y plane depending on the compounds encountered.

In each case the resulting spectrum or image can be compared by the analysis processor with the or each target spectrum (e.g. stored in the form of templates), to identify one that matches to within a predetermined threshold tolerance.

The matching process can be any suitable matching process, such as a cross-correlation between the measured data and the a target or template, or a least-means-squared error of the measured data and the target or template. The threshold tolerance then takes the form and value appropriate to the matching process.

Alternatively or in addition a parametric analysis of the positions and relative levels of peaks within the spectrum may be performed and used to identify compounds on the user's skin.

In any event, the measured data may undergo pre-processing before comparison, for example by normalisation or digital pre-filtering.

The identification of one or more predetermined compounds and their relative level or concentration in this manner can then be used to characterised the state of the user.

For example, high levels of cortisol may be indicative of stress. In this case the system may for example alter the difficulty of a game in response to this stress indicator, and/or may select to pair the user with one or more players of lower relative skill in the case of a multiplayer game.

Optionally the system may only perform such actions if there is also in-game evidence of stressors—for example if the user has not progressed past a certain point in the game within a predetermined period, or the same non-player character has killed the player's character a predetermined number of times, or a key in-game resource for the user is very low; the likely in-game indicators of stressors will vary with the game.

Similarly for example high levels of lactate may be indicative of muscle fatigue. In this case, deliberately taking longer to load a level, or suggesting that the user review their in-game inventory or otherwise takes a break from more active gameplay, may be suggested. Similarly an enemy may not be spawned, or may be spawned later, to give the user some space. Again, mitigating actions will depend on the nature of the game.

Similarly low levels of glucose in the user's sweat can indicate a low blood sugar level, which can leave the user feeling tired and shaky. Again the game can give the user a deliberate rest by altering in-game event timings, and/or alter difficulty levels, error tolerances, and the like.

Similarly, direct feedback to the user of the analysis may also be provided, for example suggesting that stressors have been detected, or signs of muscle fatigue, or that they might benefit from some rest and some food to restore blood sugars, so that they can make a conscious decision to address these matters.

More generally the system may refer to previously established correlates between the detected compound and its level, and an impact on the experience and/or performance of the user, and adapt accordingly.

As noted above, stress can be ameliorated by reducing difficulty, but stress may also have a correlation with reduced accuracy, for example; and so specifically activating an aim-assist function may be of particular help.

Similarly muscle fatigue may have a correlation with response times or posture, and so the system may prompt greater error tolerance for rhythm/dance games, or increase the size of hit boxes in a fighting game.

Again similarly low blood sugar may have a correlation with cognition, and so the system may display subtitles or instructions for longer periods to assist the user with understanding.

It will be appreciated that such correlates and/or such recommended mitigations as 'slow down presentation', 'increase accuracy tolerance' and the like may be indicated using an API or other uniform interface by the system, and a game or other application can then interpret these in a manner suitable to that game or application.

Variants

Variations on the above biometric systems and techniques may be considered, including but not limited to the following.

The optical system (either the light sensor 122 or a separate photodiode, not shown) may be used to detect when the user is holding the device, based on the degree of occlusion of ambient light. This could operate whether or not the monochromatic light source was active.

The biometric system may suspend or discard measurements whilst the handheld controller is generating haptic feedback, and/or when motion detectors of the controller indicate a shock or jerk, as such events may cause the alignment of the system to shift sufficiently to blur or corrupt the measured spectrum/image.

The biometric system may detect one or more compounds not found in sweat, such as a surfactant or other indication of soap or washing that would indicate a reset of measurements due to the removal of sweat, or that new measurements will not be useful for a period of time, or that the last valid measurements should be assumed to hold for a period of time (for example a sudden lack of glucose, cortisol, or lactate may not mean the user is no longer stressed or tired in this case, and so the mitigating actions may continue for a period).

The biometric system may use a calibration stage. This may simply detect where light falls on the light sensor so as to determine what regions to measure and which to discount as potential noise sources. It may also confirm that the optical path is correct, or indicate a need to adjust a component (for example to adjust a focus of the lens on the housing, if provided).

Alternatively or in addition, a calibration of measurements may be achieved over time based on the range of measurements observed for the one or more detected substances. This may indicate the effective detectable minimum and/or maximum for this user. These may also be associated with indicators of the correlates described elsewhere herein, for example based on user feedback, or relative performance in-game.

As noted previously herein the biometric system may be used in handheld controllers including those of videogames machines, but may also be used for other such controllers, such as controls for vehicles and industrial machinery. Similarly as noted previously herein the biometric system may be used in a head mounted display 'HMD'. The lens window for such a biometric system may be placed on a periphery of the face mask surrounding the eyes, but this is normally soft and flexible and so may make consistent placement relative to the skin difficult. Hence preferably the lens window may be placed against the forehead, either within a mounting portion of the HMD that rests on the forehead during normal use, or within a protrusion extending from the top of the face mask surrounding the eyes.

Alternatively or in addition the lens may be mounted within the face mask surrounding the eyes, and focus the monochromatic light onto a portion of skin from a distance (i.e. the skin is not in direct contact with the lens). This focussing may be automatic, and may optionally be driven by separate focussing for the presentation of images to the user's eyes, which can also use information about the relative distance of the user's face from various components of the mask. In this case the lens and the target region of skin may not be shielded from ambient light (in particular light from the HMDs own displays), and so optionally the system may only operate when the displays are not illuminated; for example, the displays may turn off whilst the user is blinking, in order to save power on illumination and possibly also on rendering of one or two unseen frames. Measurements may then be taken (or accumulated) during such blinks.

Whether implemented in a hand-held controller, head mounted display, or other user peripheral (for example a wrist-rest for a mouse or keyboard, or a gaming chair or driver's chair), an advantage of using light in the techniques described herein is that the compound detection mechanism does not need to be attached to the skin or persistently worn/mounted on the user, as would be the case with a system that relied on a chemical reaction to detect a compound. It also avoids the need for consumables (such as chemical reactants) or the need for a separate peripheral (such as a worn/mounted monitor).

As noted elsewhere herein, the detection and optionally indication of the amount or concentration of one or more compounds such as cortisol and glucose can be used to indicate the likely state of the user, for example in terms of stress and/or tiredness or blood sugar level. However optionally such readings may be used in combination with other biometric data (such as heart rate data from a wearable fitness device, and optionally medical history data (for example relating to diabetes, or tachycardia), to establish the likely state of the user with more confidence.

Alternatively or in addition, optionally such readings may be used in combination with in-app (e.g. in-game) data such as user accuracy rate, or response rate, as a function of historical user state, either specifically for the user themselves, or for typical users based on a corpus of other users (optionally filtered to be demographically and/or medically similar to the current user).

Hence a characteristic drop-off in accuracy, or a slowdown in reflexes, in conjunction with a drop in detected glucose concentrations, may be a strong indicator not just that the user has become tired, but that tiredness is impacting their likely enjoyment of the game and so in-game mitigations may be useful (such as those described elsewhere herein).

Returning now to FIGS. 3 and 4, in a summary embodiment of the present description, user input device 80, comprises at least the following: an optical window (for example lens 106 or window 106') facing onto a region of skin of the user (for example their palm or part of their face) when the user input device is in normal use; a monochromatic light source (for example laser 102) arranged to emit light through the optical window; a spectral dispersal unit (for example diffraction grating 118 or 118') adapted to disperse the spectrum of light reflected back from the region of skin of the user, the reflected light no longer being wholly monochromatic due to Raman scattering; and a light sensor (for example a CMOS imaging sensor 122, 122') operable to detect at least some of the dispersed spectrum of light and output corresponding light data.

Instances of this summary embodiment implementing the methods and techniques described herein are envisaged within the scope of the application, including but not limited to that:

In an instance of the summary embodiment, the user input device is a hand-held controller, and the optical window is mounted in a housing of the controller at a position where it is in contact with the palm of a user when the hand-held controller is in normal use, as described elsewhere herein;

In an instance of the summary embodiment, the hand-held controller is one selected from the list consisting of a hand-held videogame console, a videogame hand-held controller (such as the PlayStation DualSense®), a wand controller (such as the PlayStation Move®), a virtual reality motion controller (such as the PlayStation VR 2® controller), a mouse, a joystick (whether for a videogame console or other device or machine), and a steering wheel (whether for a videogame console or other device or machine, for example a car), as described elsewhere herein;

In an instance of the summary embodiment, the user input device is a head mounted display (such as the PlayStation VR 2®), as described elsewhere herein;

In an instance of the summary embodiment, the monochromatic light source is a laser, as described elsewhere herein;

In an instance of the summary embodiment, the optical window comprises a lens to focus the monochromatic light onto the skin of the user, as described elsewhere herein;

In an instance of the summary embodiment, the user input device comprises one or more filters situated in the light path between the optical window and the spectral dispersal unit, the one or more filters being adapted to filter one or more selected from the list consisting of light at the frequency of the monochromatic light source (e.g. to substantially mask out the source light), light at frequencies of a predetermined subset of frequencies corresponding to one or more contaminant compounds (e.g. to substantially mask out expected but unwanted compounds); and light at frequencies other than a predetermined subset of frequencies corresponding to one or more target compounds (e.g. to only mask-in one or more expected and wanted compounds), as described elsewhere herein;

Referring now also to FIG. 1, in an instance of the summary embodiment, a biometric system comprises the user input device as described elsewhere herein, and an analysis processor operable to identify one or more target compounds from the light data corresponding to the detected at least some of the dispersed spectrum of light, as described elsewhere herein;

In this instance, optionally the analysis processor is operable to estimate the amount or concentration of the one or more identified target compounds from the light data corresponding to the detected at least some of the dispersed spectrum of light, as described elsewhere herein;

In this instance, optionally the analysis processor is located in the user input device (not shown), as described elsewhere herein, and for example the user input device may then transmit an output of the analysis processor relating to the identification and optionally amount/concentration of one or more compounds to a remote device (typically a games console or other system under the control of the user);

Alternatively in this instance, optionally the analysis processor is located in a remote device (typically a games console or other system under the control of the user, but optionally a third party server), and the user input device comprises a transmitter to transmit at least some of the light data corresponding to the detected at least some of the dispersed spectrum of light, e.g. to the remote device, as described elsewhere herein; and In this instance, the biometric system may comprise a system under the control of the user via at least the user input device, and at least a first operational parameter of that system is modified (for example by the system under the control of the user, or a third party system, or a command from the controller) in response to an output of the analysis processor, as described elsewhere herein.

Figure 5:
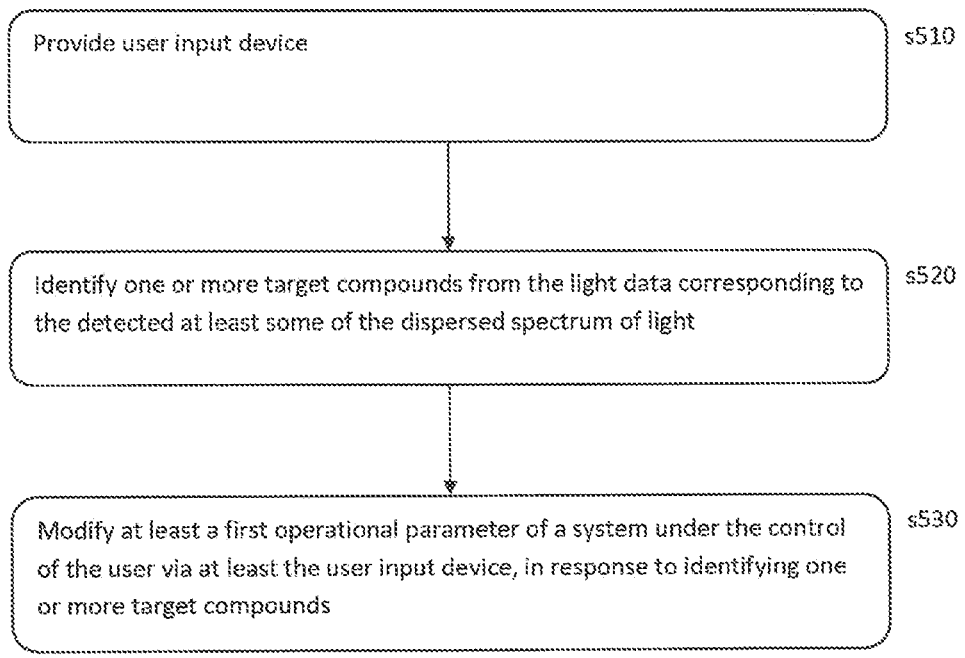
FIG. 5 is a flow diagram of a biometric method in accordance with embodiments of the present description.

Turning now to FIG. 5, in a summary embodiment of the present description a biometric method biometric method comprises the following steps. A first step s510 of providing a user input device comprising an optical window facing onto a region of skin of a user when the user input device is in normal use, a monochromatic light source arranged to emit light through the optical window, a spectral dispersal unit adapted to disperse the spectrum of light reflected back from the region of skin of the user, the reflected light no longer being wholly monochromatic due to Raman scattering, and a light sensor operable to detect at least some of the dispersed spectrum of light and output corresponding light data, as described elsewhere herein. A second step s520 of identifying one or more target compounds from the light data corresponding to the detected at least some of the dispersed spectrum of light, as described elsewhere herein. And a third step s530 of modifying at least a first operational parameter of a system under the control of the user via at least the user input device, in response to identifying one or more target compounds, as described elsewhere herein.

It will be apparent to a person skilled in the art that variations in the above method corresponding to operation of the various embodiments of the apparatus and techniques as described and claimed herein are considered within the scope of the present invention, including but not limited to that the identifying step comprises estimating an amount or concentration of the one or more identified target compounds, and the modifying step comprises modifying at least a first operational parameter of the system under control in response to the amount or concentration of one or more of the target compounds, as described elsewhere herein.

It will be appreciated that the above methods may be carried out on hardware suitably adapted as applicable by software instruction or by the inclusion or substitution of dedicated hardware, as described elsewhere herein.

Thus the required adaptation to existing parts of a conventional equivalent device may be implemented in the form of a computer program product comprising processor implementable instructions stored on a non-transitory machine-readable medium such as a floppy disk, optical disk, hard disk, solid state disk, PROM, ROM, RAM, flash memory or any combination of these or other storage media, or realised in hardware as an ASIC (application specific integrated circuit) or an FPGA (field programmable gate array) or other configurable circuit suitable to use in adapting the conventional equivalent device. Separately, such a computer program may be transmitted via data signals on a network such as an Ethernet, a wireless network, the Internet, or any combination of these or other networks.

The foregoing discussion discloses and describes merely exemplary embodiments of the present invention. As will be understood by those skilled in the art, the present invention may be embodied in other specific forms without departing from the spirit or essential characteristics thereof. Accordingly, the disclosure of the present invention is intended to be illustrative, but not limiting of the scope of the invention, as well as other claims. The disclosure, including any readily discernible variants of the teachings herein, defines, in part, the scope of the foregoing claim terminology such that no inventive subject matter is dedicated to the public.

The invention claimed is:
1. A hand held controller, comprising:
an optical window facing onto a region of skin of a user when the hand held controller is in normal use;
a monochromatic light source arranged to emit first light through the optical window;
a spectral dispersal unit adapted to: (i) receive second light received through the optical window, the second light corresponding to the first light reflected back from the region of skin of the user, the second light no longer being wholly monochromatic due to Raman scattering;

and (ii) provide a dispersed spectrum of light by dispersing a spectrum of the second light; and
a light sensor operable to detect at least some of the dispersed spectrum of the light and output corresponding light data,
wherein the optical window is mounted in a housing of the hand held controller at a position where it is in contact with a palm of a user when the hand-held controller is in normal use.

2. The hand held controller of claim 1, in which the hand-held controller is one of:
a hand-held videogame console;
a videogame hand-held controller; a wand controller;
a virtual reality motion controller; a mouse;
a joystick; and
a steering wheel.

3. The hand held controller of claim 1, in which: the monochromatic light source is a laser.

4. The hand held controller of claim 1, in which: the optical window comprises a lens to focus the monochromatic light onto the skin of the user.

5. The hand held controller of claim 1, comprising: one or more filters situated in a light path between the optical window and the spectral dispersal unit, the one or more filters being adapted to filter one or more of:
i. light at a frequency of the monochromatic light source;
ii. light at frequencies of a predetermined subset of frequencies corresponding to one or more contaminant compounds; and
iii. light at frequencies other than a predetermined subset of frequencies corresponding to one or more target compounds.

6. A biometric system, comprising:
a handheld controller having: (i) an optical window facing onto a region of skin of a user when the hand held controller is in normal use, the optical window being mounted in a housing of the hand-held controller at a position where the optical window is in contact with a palm of the user when the hand-held controller is in normal use; (ii) a monochromatic light source arranged to emit first light through the optical window; (iii) a spectral dispersal unit adapted to: (a) receive second light received through the optical window, the second light corresponding to the first light reflected back from the region of skin of the user, the second light no longer being wholly monochromatic due to Raman scattering; and (b) provide a dispersed spectrum of light by dispersing a spectrum of the second light; and (iv) a light sensor operable to detect at least some of the dispersed spectrum of the light and output corresponding light data; and
an analysis processor operable to identify one or more target compounds from the light data corresponding to the detected at least some of the dispersed spectrum of light.

7. The biometric system of claim 6, in which: the analysis processor is operable to estimate an amount or concentration of the one or more identified target compounds from the light data corresponding to the detected at least some of the dispersed spectrum of light.

8. The biometric system of claim 6, in which the analysis processor is located in the hand held controller.

9. The biometric system of claim 6, in which
the analysis processor is located in a remote device; and
the hand held controller comprises a transmitter to transmit at least some of the light data corresponding to the detected at least some of the dispersed spectrum of light.

10. The biometric system of claim 6, comprising:
a system under the control of the user via at least the hand held controller; and wherein
at least a first operational parameter of that system is modified in response to an output of the analysis processor.

11. A biometric method, comprising:
providing a hand held controller comprising: (i) an optical window facing onto a region of skin of the user when the hand held controller is in normal use, the optical window being mounted in a housing of the hand-held controller at a position where the optical window is in contact with a palm of the user when the hand-held controller is in normal use, (ii) a monochromatic light source arranged to emit first light through the optical window, (iii) a spectral dispersal unit adapted to: (a) receive second light received through the optical window, the second light corresponding to the first light reflected back from the region of skin of the user, the second light no longer being wholly monochromatic due to Raman scattering; and (b) provide a dispersed spectrum of light by dispersing a spectrum of the second light, and (iv) a light sensor operable to detect at least some of the dispersed spectrum of the light and output corresponding light data;
identifying one or more target compounds from the light data corresponding to the detected at least some of the dispersed spectrum of light; and
modifying at least a first operational parameter of a system under the control of the user via at least the hand held controller, in response to identifying one or more target compounds.

12. The biometric method of claim 11, in which
the identifying step comprises estimating an amount or concentration of the one or more identified target compounds; and
the modifying step comprises modifying at least a first operational parameter of the system under control in response to the amount or concentration of one or more of the target compounds.

13. A non-transitory, computer-readable storage medium containing a computer program comprising computer executable instructions adapted to cause a computer system to perform a method comprising:
providing a hand held controller comprising: (i) an optical window facing onto a region of skin of a user when the hand held controller is in normal use, the optical window being mounted in a housing of the hand-held controller at a position where the optical window is in contact with a palm of the user when the hand-held controller is in normal use, (ii) a monochromatic light source arranged to emit first light through the optical window, (iii) a spectral dispersal unit adapted to: (a) received second light received through the optical window, the second light reflected back from the region of skin of the user, the second light no longer being wholly monochromatic due to Raman scattering; and (b) provide a dispersed spectrum of light by dispersing a spectrum of the second light, and (iii) a light sensor operable to detect at least some of the dispersed spectrum of the light and output corresponding light data;

identifying one or more target compounds from the light data corresponding to the detected at least some of the dispersed spectrum of light; and modifying at least a first operational parameter of a system under the control of the user via at least the hand held controller, in response to identifying one or more target compounds.

\* \* \* \* \*

UNITED STATES PATENT AND TRADEMARK OFFICE
CERTIFICATE OF CORRECTION

PATENT NO. : 12,282,590 B1
APPLICATION NO. : 18/317253
DATED : April 22, 2025
INVENTOR(S) : Matthew Sanders et al.

Page 1 of 2

It is certified that error appears in the above-identified patent and that said Letters Patent is hereby corrected as shown below:

In the Claims

Column 10, Line 58: In Claim 1, delete "hand held" and insert -- handheld --.

Column 10, Line 60: In Claim 1, delete "hand held" and insert -- handheld --.

Column 11, Line 7: In Claim 1, delete "hand held" and insert -- handheld --.

Column 11, Line 8: In Claim 1, delete "hand-held" and insert -- handheld --.

Column 11, Line 10 (approx.): In Claim 2, delete "hand held" and insert -- handheld --.

Column 11, Line 11: In Claim 2, delete "hand-held" and insert -- handheld --.

Column 11, Line 12: In Claim 2, delete "hand-held" and insert -- handheld --.

Column 11, Line 13: In Claim 2, delete "hand-held" and insert -- handheld --.

Column 11, Line 18: In Claim 3, delete "hand held" and insert -- handheld --.

Column 11, Line 20: In Claim 4, delete "hand held" and insert -- handheld --.

Column 11, Line 23: In Claim 5, delete "hand held" and insert -- handheld --.

Column 11, Line 37: In Claim 6, delete "hand held" and insert -- handheld --.

Column 11, Line 39: In Claim 6, delete "hand-held" and insert -- handheld --.

Column 11, Line 41: In Claim 6, delete "hand-held" and insert -- handheld --.

Signed and Sealed this
Twenty-fourth Day of June, 2025

Coke Morgan Stewart
*Acting Director of the United States Patent and Trademark Office*

CERTIFICATE OF CORRECTION (continued)
U.S. Pat. No. 12,282,590 B1

Column 11, Line 65: In Claim 8, delete "hand held" and insert -- handheld --.

Column 12, Line 1: In Claim 9, delete "hand held" and insert -- handheld --.

Column 12, Lines 6-7: In Claim 10, delete "hand held" and insert -- handheld --.

Column 12, Line 12 (approx.): In Claim 11, delete "hand held" and insert -- handheld --.

Column 12, Line 14 (approx.): In Claim 11, delete "hand held" and insert -- handheld --.

Column 12, Line 15 (approx.): In Claim 11, delete "hand-held" and insert -- handheld --.

Column 12, Line 18 (approx.): In Claim 11, delete "hand-held" and insert -- handheld --.

Column 12, Lines 36-37 (approx.): In Claim 11, delete "hand held" and insert -- handheld --.

Column 12, Line 51: In Claim 13, delete "hand held" and insert -- handheld --.

Column 12, Line 53: In Claim 13, delete "hand held" and insert -- handheld --.

Column 12, Line 54: In Claim 13, delete "hand-held" and insert -- handheld --.

Column 12, Line 56: In Claim 13, delete "hand-held" and insert -- handheld --.

Column 13, Line 5: In Claim 13, delete "hand held" and insert -- handheld --.